US012714402B2

(12) United States Patent
Levy et al.

(10) Patent No.: US 12,714,402 B2
(45) Date of Patent: Aug. 25, 2026

(54) SYSTEMS AND METHODS FOR EFFECTIVE DELIVERY OF MONOCLONAL ANTIBODIES TO NEUROLOGICAL TARGETS

(71) Applicant: Insightec, Ltd., Tirat Carmel (IL)

(72) Inventors: Yoav Levy, Haifa (IL); Eyal Zadicario, Tel Aviv (IL); Avinoam Bar-Zion, Haifa (IL); Michael Plaksin, Tirat Carmel (IL)

(73) Assignee: Insightec Ltd., Tirat Carmel (IL)

( * ) Notice: Subject to any disclaimer, the term of this patent is extended or adjusted under 35 U.S.C. 154(b) by 1 day.

(21) Appl. No.: 18/718,320

(22) PCT Filed: Dec. 8, 2022

(86) PCT No.: PCT/IB2022/000747

§ 371 (c)(1),
(2) Date: Jun. 10, 2024

(87) PCT Pub. No.: WO2023/105288

PCT Pub. Date: Jun. 15, 2023

(65) Prior Publication Data

US 2025/0040912 A1 Feb. 6, 2025

Related U.S. Application Data

(60) Provisional application No. 63/287,909, filed on Dec. 9, 2021.

(51) Int. Cl.
*A61B 8/08* (2006.01)
*A61B 8/00* (2006.01)

(52) U.S. Cl.
CPC .......... *A61B 8/5223* (2013.01); *A61B 8/0891* (2013.01); *A61B 8/481* (2013.01); *A61B 8/5207* (2013.01)

(58) Field of Classification Search
CPC ..... A61B 8/5223; A61B 8/0891; A61B 8/481; A61B 8/5207
See application file for complete search history.

(56) References Cited

U.S. PATENT DOCUMENTS

| | | | | |
|---|---|---|---|---|
| 2008/0008657 | A1* | 1/2008 | Bussat | A61K 49/223 424/9.52 |
| 2018/0353242 | A1* | 12/2018 | Yoshikawa | G06T 7/0012 |
| 2021/0187331 | A1* | 6/2021 | Zadicario | A61N 7/02 |
| 2022/0288227 | A1* | 9/2022 | Chattaraj | A61K 9/5031 |

OTHER PUBLICATIONS

International Search Report and Written Opinion for related International Patent Application No. PCT/IB2022/000747, dated May 3, 2023, 11 pages.

Choi J Jet al: "Microbubble-Size Dependence of Focused Ultrasound-Induced Blood-Brain Barrier Opening in Mice In Vivo", IEEE Transactions on Biomedical Engineering, IEEE, USA, vol. 57, No. 1, Jan. 1, 2010 (Jan. 1, 2010).

* cited by examiner

*Primary Examiner* — Kaitlyn E Sebastian
(74) *Attorney, Agent, or Firm* — Morgan, Lewis & Bockius LLP

(57) ABSTRACT

Systems and methods are provided for initializing an ultrasound procedure for a target region. The method includes determining a distribution of vessel diameters of vasculature in a target region. The method also includes providing, at the target region, microbubbles having a size distribution related to the distribution of vessel diameters.

20 Claims, 5 Drawing Sheets

200

Frequency 202

0 2 4 6 8 10 12

10-20 20-30 30-40 40-50 50-60

Size of Blood Vessels
204 (microns)

206

Frequency 208

0 1 2 3 4 5 6

0-10 10-20 20-30 30-40 40-50

Size of Microbubbles
210 (microns)

SYSTEMS AND METHODS FOR EFFECTIVE DELIVERY OF MONOCLONAL ANTIBODIES TO NEUROLOGICAL TARGETS

RELATED APPLICATION

This application is a 371 National Stage Entry of International Patent Application No. PCT/IB2022/000747 filed Dec. 8, 2022, which claims the benefit of and priority to U.S. Provisional Patent Application No. 63/287,909 (filed on Dec. 9, 2021), the entire disclosure of which is hereby incorporated by reference.

FIELD OF THE INVENTION

The present invention relates, generally, to ultrasound procedures, and more particularly to systems and methods for initializing an ultrasound procedure for a target region while avoiding damage to healthy tissue.

BACKGROUND

Monoclonal antibodies (mABs) are used with increasing success against many tumors but, for brain tumors, the blood-brain barrier (BBB) is a special concern. The BBB prevents antibody entry to the normal brain. This is attributed to the size of the mABs, which generally are in the range of 15 kDa. The tumor may itself partially disrupt the BBB, enabling some mABs to enter the tumor. However, particularly at the periphery of the tumor, where cancer cells may already be infiltrating into normal brain tissue and mAb delivery may be most beneficial therapeutically, the BBB remains intact.

Various approaches to reversible, targeted BBB disruption have been demonstrated in the past few decades, including the use of focused ultrasound. Using focused ultrasound has various benefits. For example, the disruption can be localized to a target area, the disruption can be performed through an intact skull, and the disruption can be controlled so it is transient and without severe side effects. BBB disruption with ultrasound typically involves administration of microbubbles so they reach the target region. The mechanical oscillations of these microbubbles caused by the ultrasound disrupt the BBB. However, severe oscillations may cause hemorrhages and minor oscillations may not provide sufficient BBB disruption. Current techniques may use acoustic feedback to monitor that the oscillations are within a safe and effective margin. However, there may be no guarantee that these oscillations represent bubble activity at the target area—they may be coming from anywhere in the brain.

There are other limitations when using microbubbles to disrupt the BBB. The microbubbles cannot enter blood vessels in the brain whose diameters are smaller than those of the microbubbles; for example, typical microbubbles may have diameters on the order of microns, whereas microcapillaries at the tumor sites may be only nanometers wide. This means that the applied ultrasound may not affect a significant fraction of the intact BBB at the tumor site. Conversely, treatments conducted using microbubbles in the nanometer diameter range (also known as nanobubbles) might not be effective in causing BBB disruption when the target area is populated by larger blood vessels. Accordingly, there is a need for approaches that efficiently introduce microbubbles throughout the vasculature of BBB sites to be disrupted using ultrasound procedures.

SUMMARY

In accordance with embodiments of the present invention, the distribution of vessel diameters of vasculature in a target region is determined and microbubbles having a similar size distribution are introduced prior to or concomitant with therapeutic application of ultrasound. The similar size distributions ensure that the microbubbles will penetrate a sizable fraction of the vasculature, enhancing the efficiency of BBB disruption when ultrasound energy is applied. The vasculature may be characterized (e.g., to determine the distribution of vessel diameters) using an atlas, contrast-enhanced ultrasound, ultrasound super-resolution imaging, ultrasound localization microscopy, magnetic resonance imaging (MRI), computed tomography (CT) or other suitable modality.

In a first aspect, therefore, the invention relates to a system for initializing an ultrasound procedure for a target region. In various embodiments, the system comprises an ultrasound transducer and a controller configured to determine a distribution of vessel diameters of vasculature in a target region and provide, at the target region, microbubbles having a diameter size distribution related to the distribution of vessel diameters—e.g., a bubble:vessel diameter ratio ranging from 1:2 to 1:30 (so that for a 30 μm vessel, the optimal bubble diameter is 1-15 μm). Typically the diameter ratio is considered over a range of diameters, e.g., corresponding to histogram bin ranges. Within each such bin range, the relative populations of bubbles and vessels (the histogram heights) preferably differ significantly, with many more microbubbles than corresponding vessels. The population ratio of microbubbles sized for a particular vessel size (or size range) may be as low as $10^2$ and as high as $10^9$. Hence, if the average vessel size of a histogram bin is 30 μm, the average microbubble size of the corresponding histogram bin may be 2 μm, and while the pattern of vessel and microbubble histogram bins may be similar (or even identical), the heights of corresponding bins will be significantly different, i.e., there will be many more bubbles than vessels. In some embodiments bubble size distribution is expressed in concentration. In some embodiments, concentration is the concentration in the bubbles mix or the estimated concentration in the target tissue or the concentration in the patient blood.

It should be understood, however, that the relationship between bubble and vessel diameters may be more complex than a simple ratio. For example, the relationship may be polynomial, exponential or determined empirically. Alternatively or in addition, the microbubble size distribution may be a function of the type of microbubble. In some embodiments, a vessel volume distribution is generated by the controller and the bubble distribution is selected based on the volume information. Alternatively or in addition, only few prominent bins (e.g., two to five bins) from the vessel size distribution may be selected and other bins ignored. In some embodiments, the bubble distribution for each of the prominent bins is equal or approximately equal. In some embodiments, the bubble distribution is represented in terms of bubble volume (i.e., the volume of all of the bubbles within each size range).

In some embodiments, the distribution of vessel diameters and the microbubble size distribution are histogram distributions having equal (or substantially equal) numbers of bins. For example, the distribution of vessel diameters and the microbubble size distribution may be histogram distributions having a substantially similar pattern of peaks even if the absolute heights of corresponding peaks differ. The microbubbles may be generated by application of ultrasound at the target region or by administration as a suspension. Microbubbles in the sub-micron range can also be administered as phase-shift nano-droplets.

In some embodiments, the target is the blood-brain barrier. The vessels may be cortical vessels that range in diameter from 4 μm (capillaries) to less than 100 μm (arteries/veins). For example, the distribution of vessel diameters may have a peak at approximately 50 μm. The vessel size range of the relevant vasculature may be established by imaging the target region, e.g., using magnetic resonance imaging (MRI) or other suitable imaging modality. Alternatively, once the target region is identified, an atlas may be used to determine the distribution of vessel diameters.

In some embodiments, the controller is further configured to determine at least one parameter associated with the ultrasound transducer for controlling acoustic energy emitted by transducer elements so that the acoustic energy is above a threshold level to thereby induce microbubble generation. The parameter(s) associated with the ultrasound transducer may consist of or include frequency, amplitude and/or phase associated with one or more elements of the ultrasound transducer.

In some embodiments, the system further includes means for detecting a characteristic of the microbubbles in the target region. The detecting means may include or consist of the ultrasound transducer, an acoustic-signal detection device or a second ultrasound transducer. In some embodiments, the characteristic may be or include the presence, concentration and/or amount, and/or behavior or response (e.g., cavitation), of the microbubbles. The controller may be configured to determine at least one parameter associated with the ultrasound transducer based at least in part on the detected characteristic of the microbubbles.

As used herein, the terms "approximately" and "substantially" mean±20%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
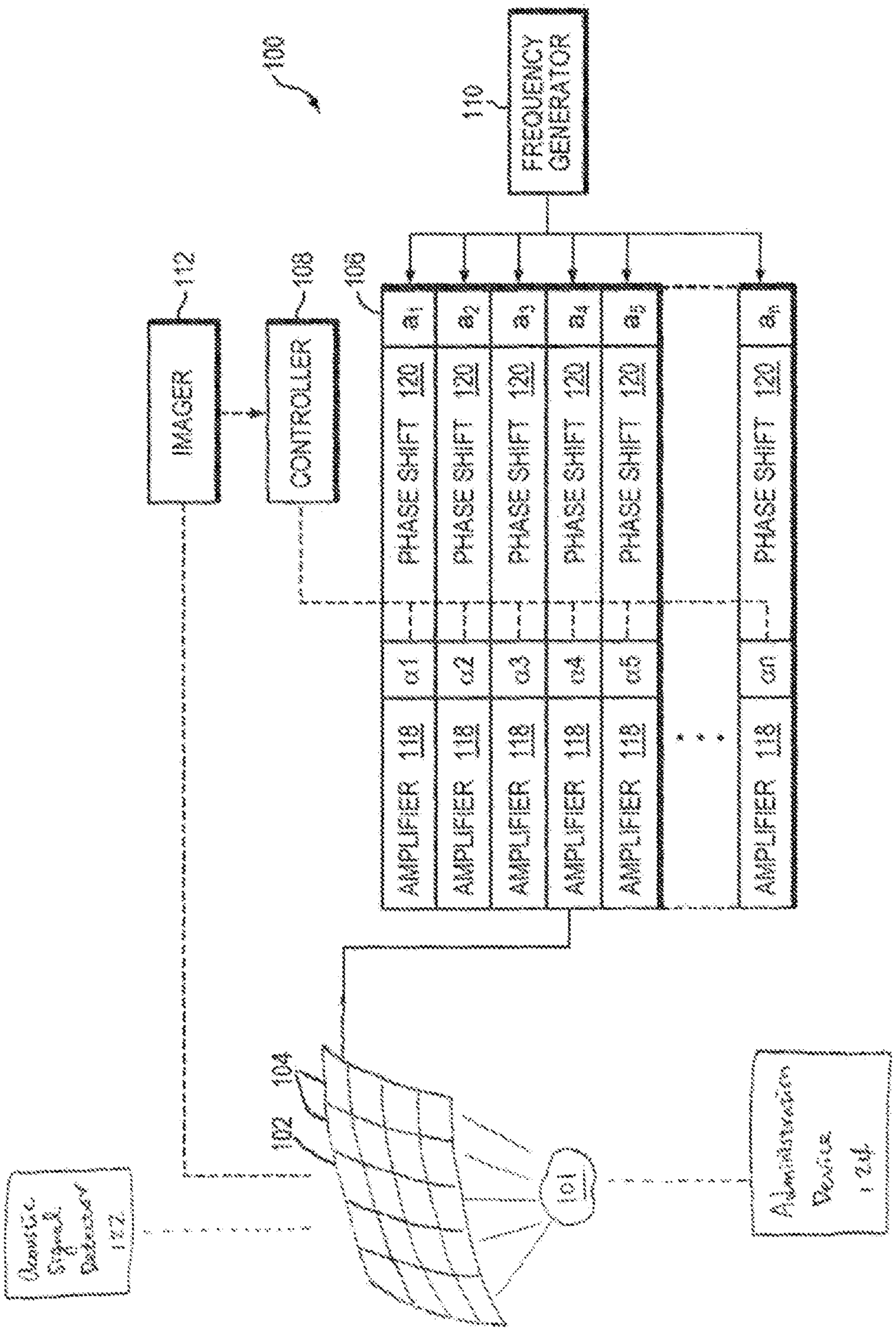
FIG. 1 schematically depicts an exemplary ultrasound system in accordance with various embodiments of the current invention.

FIG. 1 illustrates an exemplary ultrasound system 100 for generating and delivering a focused acoustic energy beam to a target region 101 within a patient's body. The applied ultrasound waves may be reflected from the target region and/or non-target region, and an image of the target and/or non-target regions may be generated based on the reflected waves. In addition, microbubbles may be introduced to the target region 101 and/or non-target region to increase ultrasound reflections, thereby improving the contrast of the ultrasound image. In some embodiments, the applied ultrasound waves may ablate tissue in the target region 101 and/or induce microbubble oscillation and/or cavitation to improve treatment effects. The illustrated system 100 includes a phased array 102 of transducer elements 104, a beamformer 106 driving the phased array 102, a controller 108 in communication with the beamformer 106, and a frequency generator 110 providing an input electronic signal to the beamformer 106. In various embodiments, the system further includes an imager 112, such as a magnetic resonance imaging (MRI) device, a computer tomography (CT) device, a positron emission tomography (PET) device, a single-photon emission computed tomography (SPECT) device, or an ultrasonography device, for determining anatomical characteristics (e.g., the type, property, structure, thickness, density, etc.) of the tissue at the target region 101 and/or the non-target region.

The array 102 may have a curved (e.g., spherical or parabolic) shape suitable for placement on the surface of the patient's body, or may include one or more planar or otherwise shaped sections. Its dimensions may vary between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at, e.g., 50Ω to match (or substantially match) input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each including or consisting of an amplifier 118 and a phase delay circuit 120; each drive circuit drives one of the transducer elements 104. The beamformer 106 receives a radio frequency (RF) input signal, typically in the range from 0.1 MHz to 10 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $\alpha_1$-$\alpha_n$ imposed by the beamformer 106 serve to transmit and focus ultrasonic energy through the intervening tissue located between the transducer elements 104 and the target region onto the target region 101, and account for wave distortions induced in the intervening tissue. The amplification factors and phase shifts are computed using the controller 108, which may provide the computational functions through software, hardware, firmware, hardwiring, or any combination thereof. In various embodiments, the controller 108 utilizes a general-purpose or special-purpose digital data processor programmed with software in a conventional manner, and without undue experimentation, in order to determine an optimal value of an ultrasound parameter (e.g., a frequency, a phase shift and/or an amplification factor) associated with each element 104 so as to generate a desired focus or any other desired spatial field patterns. The optimal value of the ultrasound parameter may be refined experimentally before, after, and/or at one or more times during the ultrasound procedure based on, for example, the focus quality, the focus location relative to the target 101 and/or the microbubble response to the ultrasound sonications. The quality and location of the focus may be monitored using the imager 112, and the microbubble response may be detected using the transducer 102 and/or an acoustic-signal detector 122 (e.g., a hydrophone).

In certain embodiments, the optimal value of the ultrasound parameter is computationally estimated based on detailed information about the characteristics of the intervening tissue and their effects (e.g., reflection, refraction, and/or scattering) on propagation of acoustic energy. Such information may be obtained from the imager 112 and analyzed manually or computationally. Image acquisition may be three-dimensional or, alternatively, the imager 112 may provide a set of two-dimensional images suitable for reconstructing a three-dimensional image of the target and/or non-target regions. Image-manipulation functionality may be implemented in the imager 112, in the controller 108, or in a separate device.

In certain treatment scenarios, ultrasound waves propagating towards the target region 101 from different directions may encounter a highly variable anatomy, such as different thicknesses of tissue layers and different acoustic impedances; as a result, energy deposition at the target region 101 varies significantly and often nonmonotonically with frequency, and the optimum frequency for a particular patient is typically unpredictable. Accordingly, in some embodiments, the frequency of the ultrasound is optimized by sequentially sonicating the target region 101 with waves having different "test frequencies" within a test frequency range; for each tested frequency, a parameter (e.g., temperature, acoustic force, tissue displacement, etc.) indicative of energy deposition in the target region 101 is measured. The test range may span the entire range of frequencies suitable for ultrasound treatment (e.g., in various embodiments, 0.1 MHz to 10 MHz), but is typically a much smaller sub-range thereof within which the optimal frequency is expected. Such a sub-range may be determined, e.g., based on computational estimates of the optimal frequency, the results of simulations, or empirical data acquired for the same target in other patients. Further details about determining the optimal frequency for the ultrasound application are provided, for example, in U.S. Patent Publication No. 2016/0008633, the entire content of which is incorporated herein by reference.

In some embodiments, optimizing the ultrasound frequency involves iteratively setting a test frequency, sonicating the target region 101 at the selected frequency, and quantitatively assessing the resulting focusing properties or energy deposition at the target region 101. This may be accomplished using, e.g., MRI thermometry to measure the temperature increase in the target region 101 resulting from the deposited energy, MR-ARFI to measure the tissue displacement resulting from the acoustic pressure at the target region 101, ultrasound detection to measure the intensity of the ultrasound reflected from the target region 101, or generally any experimental technique for measuring a parameter that correlates with energy deposition at the target region 101 in a known and predictable manner. Following frequency optimization, the phase and/or amplitude settings of the phased-array transducer 102 may be adjusted to optimize the focus for the selected frequency. Approaches to assessing focusing properties at the target region 101 and, based thereon, adjusting the ultrasound frequency, phase and/or amplitude settings of the phased-array transducer 102 are provided, for example, in an International Patent Application entitled "Adaptive, Closed-Loop Ultrasound Therapy" filed on even date herewith, the entire disclosure of which is hereby incorporated by reference.

In various embodiments, microbubbles and/or other therapeutic agents are introduced intravenously or, in some cases, by injection proximate to the target region 101 using an administration system 124 for enhancing the ultrasound procedure on the target region. For example, the microbubbles may be introduced into the patient's brain in the form of liquid droplets that subsequently vaporize, or as gas-filled bubbles, or entrained with another suitable substance, such as a conventional ultrasound contrast agent. Because of their encapsulation of gas, the microbubbles may act as scatterers/harmonic oscillators or reflectors of the ultrasound. Reflections from the microbubbles may be more intense than the reflections from the soft tissue of the body and/or blood. Therefore, by using a microbubble-based contrast agent, the contrast level of an ultrasound image may be significantly increased.

In addition, the microbubbles may react to an applied oscillating acoustic pressure with volume pulsations. Depending on the amplitude of the ultrasound waves, microbubble oscillation will be related either linearly or nonlinearly to the applied acoustic pressure. For a relatively low acoustic pressure, the instantaneous radius of the microbubbles may oscillate linearly in relation to the amplitude of the applied acoustic pressure. Microbubble oscillation is governed by parameters such as the resonance frequency, damping coefficients, and shell properties. Thus, if the frequency of the applied acoustic waves is equal to the microbubble resonance frequency, the microbubbles may experience a large force and can collapse. This may result in undesired damage to the non-target tissue if the microbubbles are present therein.

To avoid this undesired effect, in various embodiments, the resonance frequency of the microbubbles is selected to be substantially different from (e.g., two times greater than) the selected optimal ultrasound frequency. In addition, the transducer elements 104 are activated to transmit waves having a low acoustic power (e.g., 5 W) during treatment. In this way, because the ultrasound waves arriving the non-target region have a low acoustic intensity and their frequency is substantially different from the resonance frequency of the microbubbles, the microbubbles in the non-target region may be unresponsive (or have a limited response without cavitation) to the applied acoustic field. This ensures that no (or at least a very limited amount of) non-target tissue is damaged. In contrast, at the target region 101, where the ultrasound beams are focused, the acoustic intensity is substantially larger than that outside the target region and may be sufficient to cause the microbubbles to oscillate and/or collapse. This may enhance energy absorption at the target region 101 for tissue ablation and/or cause disruption of blood vessels for targeted drug delivery.

In some embodiments, the administration system 124 adjusts one or more characteristics of the microbubbles according to the tissue type. In some embodiments, the administration system 124 selects a mixture of microbubbles for a particular tissue, e.g., with a size distribution similar (e.g., substantially similar) to the distribution of blood-vessel sizes in the tissue. The microbubble mixture, sometimes called a TUB (therapeutic ultrasound bubble), thereby diffuses throughout the vasculature of the target region so that, for example, disruption may occur in the gross surroundings of the tumor as well as in the small capillaries of microtumor sites. More generally, based on the tissue to be treated or on treatment feedback, an optimal mixture of bubble types is used for a treatment or a continuation of a treatment. Bubble types may be selected based on one or more of the following tissue parameters: (i) mechanical properties such as elasticity, (ii) tissue resiliency to treatment, (iii) biological properties (e.g., affinity to bubbles), (iv) the distribution of diameters of blood vessels. In addition, feedback (e.g., acoustic response and/or MRI imaging to reveal tissue permeability) received during treatment may suggest changes to the bubble mixture composition. Relevant feedback parameters include (i) acoustic response (e.g., the power spectrum of the tissue response), (ii) MRI imaging (e.g., contrast enhancement homogeneity), and (iii) immediate or delayed physiological response. For example, if the physiological or acoustic response or the contrast enhancement homogeneity is too low or too high, the microbubbles may be replaced with a mixture exhibiting a higher or lower response to acoustic energy.

In various embodiments, the following characteristics may differentiate bubble types: (i) shell composition, (ii) gas composition, (iii) size, (iv) preparation procedure, and (v) "piggyback" materials (e.g., MRI contrast agents, targeting bodies). Microbubble preparations with different shell and gas compositions are available commercially and may, for example, be stored in different compartments of the administration system 124. In response to changing values of feedback parameters, the controller 108 may alter the mix of bubbles supplied by the administration system 124 during treatment. The same principle may be used to achieve a desired microbubble size distribution. As described in International Application No. PCT/IB2018/001537 (filed on Dec. 5, 2018), the entire disclosure of which is hereby incorporated by reference, a desired microbubble size distribution may be achieved by selective filtration and administration. Alternatively, the administration system 124 may have compartments containing commercially available microbubble preparations with different size distributions. These may be combined in various proportions by simultaneous or sequential administration to achieve a desired size distribution. In addition, techniques such as decantation, centrifugation, and pore-filtration may be used to isolate microbubble sizes from the native, commercially obtained contrast agent (see, e.g., Cheung et al., In vitro characterization of the subharmonic ultrasound signal from definity microbubbles at high frequencies," *Phys. Med. Biol.* 53, 1209-1223 (2008); Feshitan et al., "Microbubble size isolation by differential centrifugation," *J. Colloid Interface Sci.* 329, 316-324 (2009)). In addition, as described in Shekhar et al., "Modifying the size distribution of microbubble contrast agents for high-frequency subharmonic imaging," *Med. Phys., August* 2013, 40(8): 082903, the time evolution of microbubble size may be used to create contrast agents with lower median sizes than the native agent. The foregoing references are incorporated by reference herein in their entireties.

It should be stressed that microbubbles represent one example of treatment enhancers. Alternatively or in addition, nanodroplets or nanoparticles such as gold seeds may be employed. Furthermore, the term "mixture" as used herein is generally understood to connote a combination of bubble types administered together. However, in some embodiments, a mixture includes different types of bubbles administered sequentially. Sometimes, the activity of one bubble type is prerequisite to the success of another bubble type used simultaneously or thereafter. These and other aspects of administration of microbubbles are described further below with reference to FIGS. 2 and 3A-3C.

Figure 2:
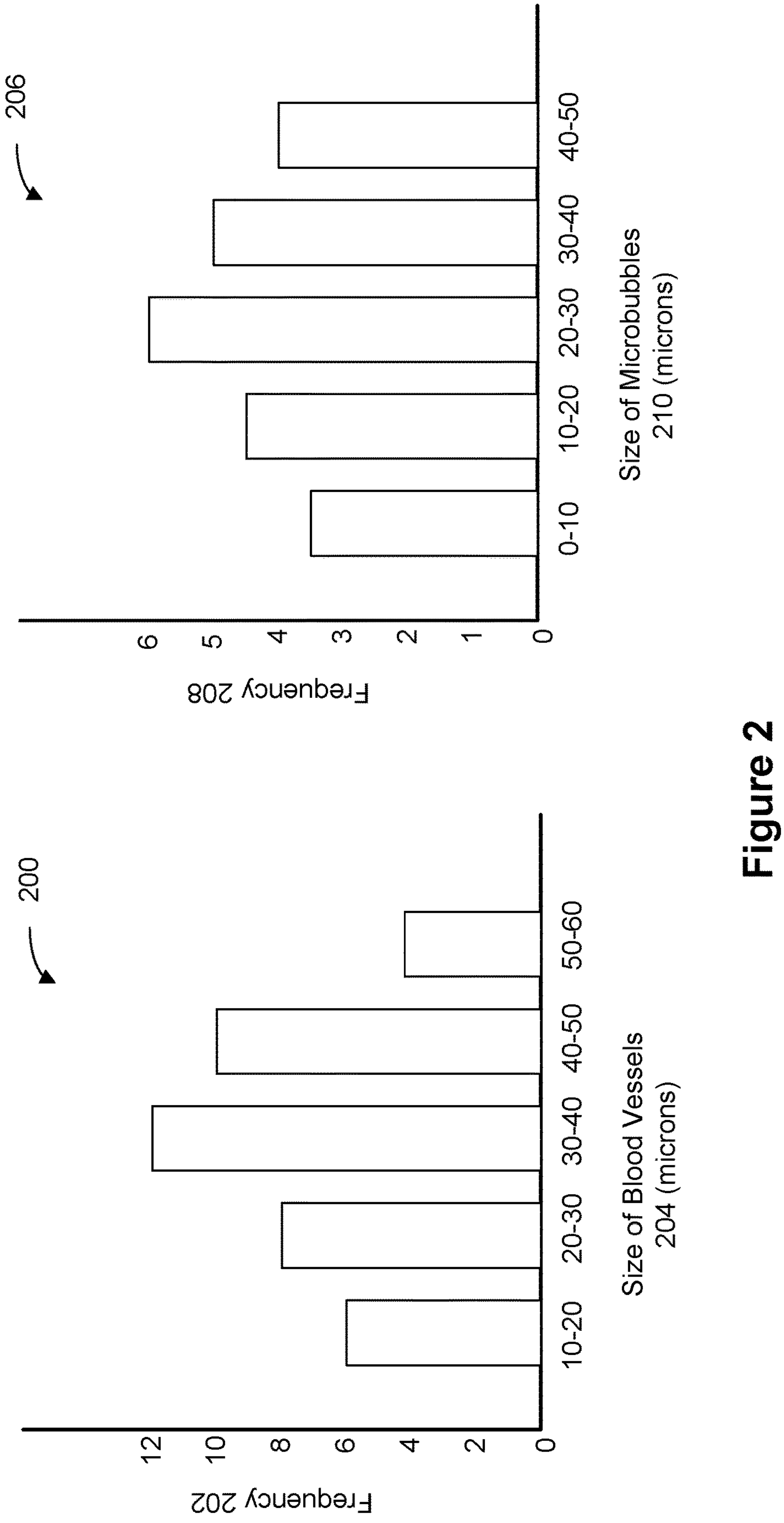
FIG. 2 shows example histograms for vessel sizes and microbubble sizes.

FIG. 2 shows example binned distributions for vessel sizes and microbubble sizes in accordance with some embodiments. The histogram 200 corresponds to a distribution of sizes (i.e., diameters) of blood vessels (μm) 204, and the histogram 206 corresponds to a distribution of sizes (i.e., diameters) of microbubbles 210 generated based on the distribution shown in the histogram 200. The y-axes 202 and 208 correspond to the frequencies (or, in some cases, the absolute numbers) of blood vessels and microbubbles, respectively, in each size bin. For ease of presentation, histogram heights for blood vessels and microbubbles are shown as equal; as explained above, however, the heights of the microbubble histogram bins would be much greater than those of the vessel histogram bins (e.g., by a factor of $10^2$ to $10^9$). Furthermore, these example values are shown for illustrative purposes, and should not be construed as restricting the choice of the size values. In particular, the range of sizes of blood vessels may vary for different tissues, or even for the same tissue for different patients. Similarly, the number of bins or buckets (five in the example shown) may differ for each embodiment, different tissues, and/or different patients. The number of size bins appropriate to a particular application is straightforwardly determined without undue experimentation, and will typically depend most prominently on the width of the blood-vessel size distribution and the degree of control that may be exerted over the microbubble size distribution. Because the objective is to enhance overall efficiency rather than precisely populate blood vessels with equal numbers of microbubbles, the overall distribution pattern is more important than the number of bins. In some instances, as few as two bins may suffice, while broad size distributions call for a greater number (e.g., five, as shown, or 10 or more) of bins. It should be stressed that, in practice, the distribution patterns need not match exactly; in fact, errors in matching up to 50% can be tolerated.

Furthermore, the number of bins or buckets shown on the histogram 206 need not match the number of bins in the histogram 200. In other words, the mapping from one histogram to the other histogram need not be one-to-one, and multiple buckets in one histogram 200, 206 may be mapped to the same bucket in the other histogram. In this way, different embodiments can optimize for different situations depending on factors such as tissue type, size, and location, the feasibly obtainable precision of the microbubble size distribution, and so on. Some embodiments generate substantially similar distributions via the mapping described above. The histogram profiles shown in FIG. 2 generally follow a Gaussian distribution with a peak height, but this need not be the case. Instead, the size distribution may instead be linear, flat, decrease exponentially from a peak value, or follow another pattern. But the overall objective remains to align the distribution of microbubble sizes with that of blood-vessel sizes according to a predetermined relationship.

That relationship may be linear—e.g., the ratio of microbubble diameters to corresponding vessel diameters ranging from 1:2 to 1:30; in the figure, again for ease of presentation, the ratio is approximately 1:2 across bins. In other embodiments, the predetermined relationship is polynomial, exponential or determined empirically. To determine the relationship empirically, mixtures having different narrow bubble distributions may be employed in different experiments. In each experiment, the dominant vessel size in each area is compared to the opening measured by a marker (e.g., Gadolinium in MRI) and the best-performing bubble mixture is determined, thereby revealing the optimal approximate microbubble diameter. Mixtures with similar size distributions but different concentrations may be employed to establish the optimal bubble-to-vessel ratio for the optimal bubble size. To treat a large area having a wide distribution of vessel sizes, combinations of bubble mixtures may be employed based on the empirically established size and concentration relationships for each vessel size.

Alternatively or in addition, the microbubble size distribution may be a function of the type of microbubble. The shell type and gas type, for example, strongly affect how an acoustic field interacts with the bubbles.

Additionally, the overall ratio of microbubbles to correspondingly sized blood vessels may be determined empirically, and may be tailored for different applications, for different antibodies or drugs, and so on. An example representative size range for microbubbles is 0.5-20 μm with a peak at, e.g., 1-5 μm.

Figure 3A:
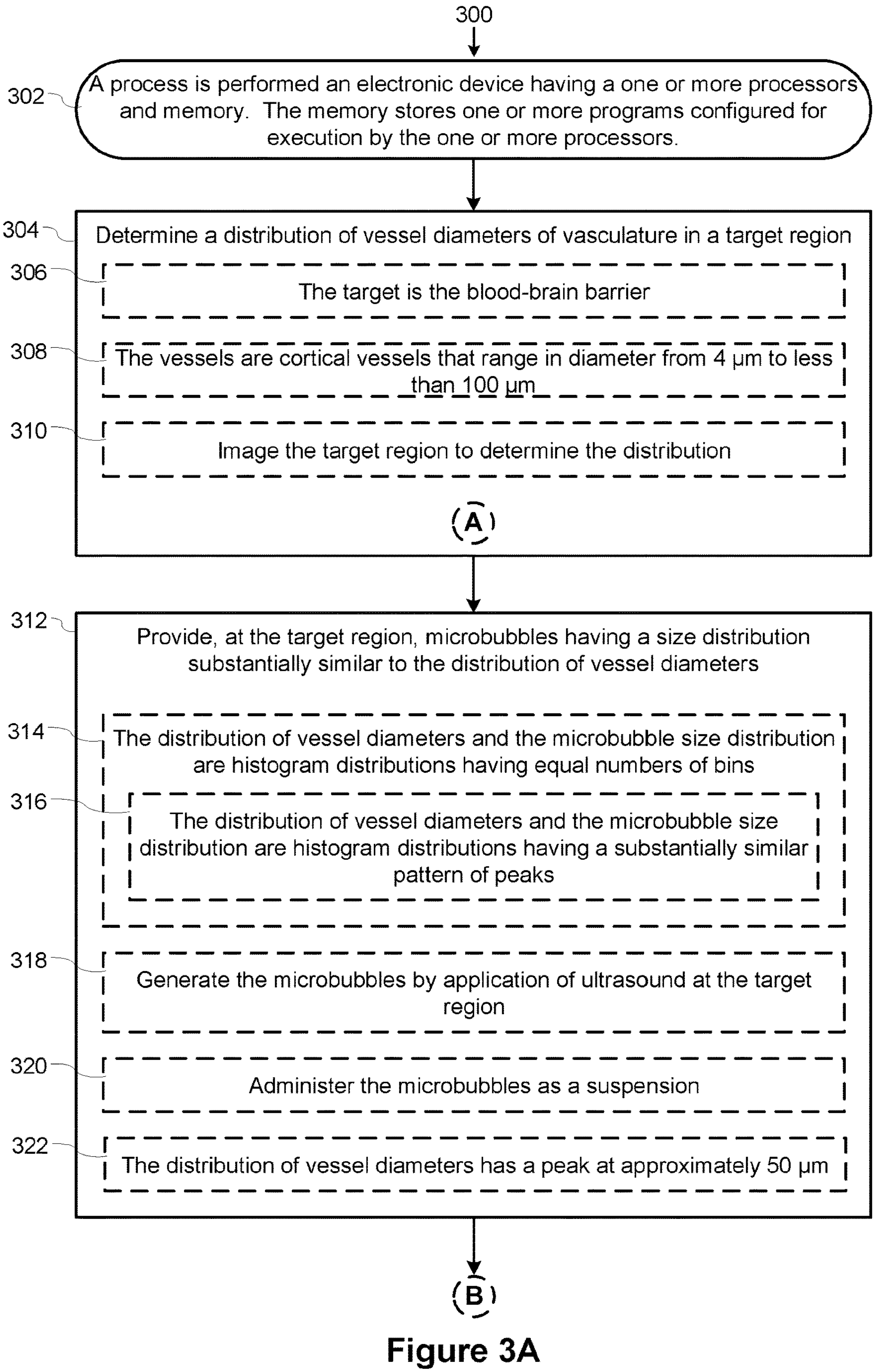
FIGS. 3A-3C show a flowchart of an example method for initializing an ultrasound procedure for a target region, according to some embodiments.
Figure 3B:
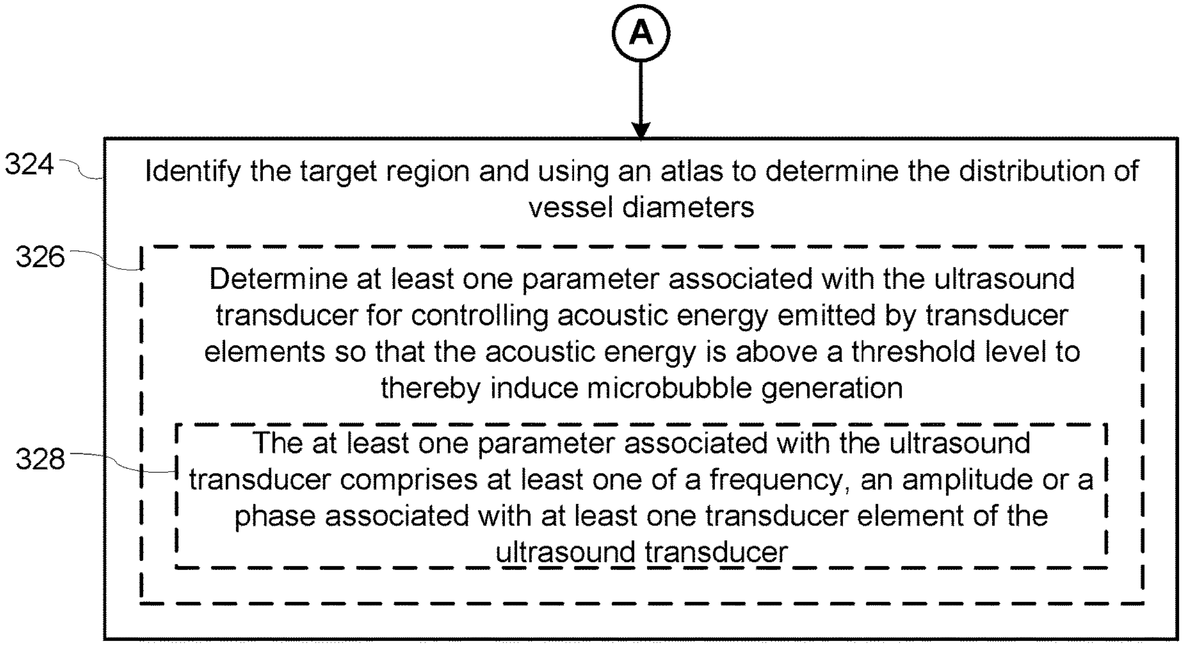
Figure 3C:
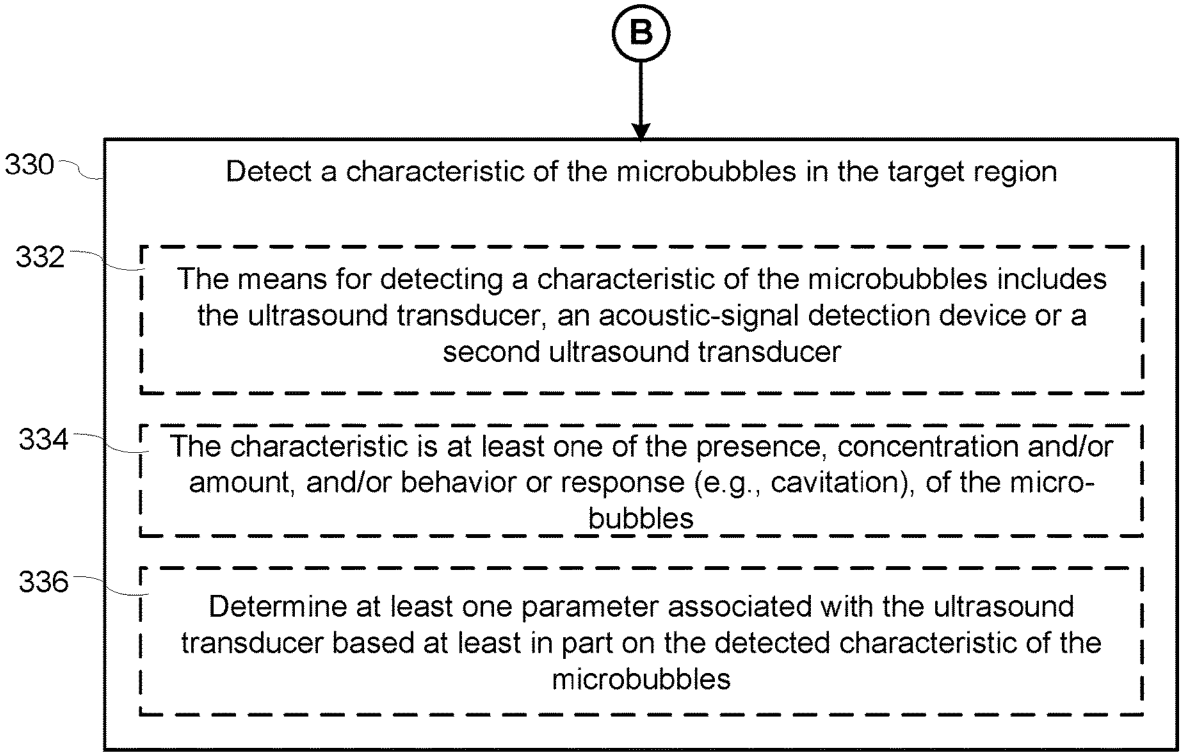

FIGS. 3A-3C show a flowchart of an example method 300 for initializing an ultrasound procedure for a target region, according to some embodiments. The method (or process) may be performed at an electronic device having a one or more processors and memory (step 302). The memory stores one or more programs configured for execution by the one or more processors. The method may be performed by a controller, such as the controller 108, an administration system or administration device 124, a combination of components, or some or all of the components of the system 100 described above in reference to FIG. 1. The controller 108 or the administration device 124 may be configured to perform any of the methods described herein, according to some embodiments.

As shown in FIG. 3A, the method 300 includes determining a distribution of vessel diameters of vasculature in a target region (step 304). In some embodiments, the target includes a portion of the blood-brain barrier (step 306). For example, the vessels may be cortical vessels that range in diameter from 4 μm to less than 100 μm (step 308). In some embodiments, the determining step includes imaging the target region (step 310), e.g., using contrast MRI/Doppler ultrasound or MRI perfusion (based, in the latter case, on a known correlation between the perfusion rate and vessel size).

Referring next to FIG. 3B, in some embodiments, the determining step 304 includes identifying (step 324) the target region and using an atlas (which may be a standard reference, e.g., Mouches et al., "A statistical atlas of cerebral arteries generated using multi-center MRA datasets from healthy subjects," Scientific Data 6, Art. No. 29 (2019), which is incorporated herein by reference) to determine the distribution of vessel diameters. Alternatively, the vessel sizes may be characterized by MRI or other tomographic imaging technique; successive tomographic slices representative of the target tissue are analyzed and vessel-diameter statistics determined computationally. Next, at least one parameter associated with the ultrasound transducer for controlling acoustic energy emitted by transducer elements is determined (step 326) so that the acoustic energy is above a threshold level to induce microbubble generation and/or cavitation. In some embodiments, the parameter(s) associated with the ultrasound transducer include (step 328) frequency, amplitude and/or phase, and the parameter(s) will typically differ among separately driven transducer elements of the ultrasound transducer.

In other embodiments, contrast-enhanced ultrasound (CEUS) or ultrasound super-resolution imaging (e.g., using ultrasound localization microscopy or ULM) to generate vascular maps; see, e.g., PCT Publ. No. WO 2021/123905 and Errico et al., "Ultrafast ultrasound localization microscopy for deep super-resolution vascular imaging," *Nature,* 527(7579), 499-502 (2015), the entire disclosures of which are hereby incorporated by reference. In the case of CEUS, harmonic or temporally changing echoes are known to come from intravascular bubbles. After producing a spatial map of the bubbles in each frame CEUS image frame, in a process known as beamforming, irrelevant tissue-related noise is removed from the desired bubble signals. CEUS processing includes denoising of the beam-formed bubble images over time to produce a clear, low-resolution image of the vasculature. ULM processing includes finding the exact locations of resolvable bubbles and aggregating this information over a succession of frames to produce a super-resolved image of the vasculature. High and/or low microbubble concentration, long (ms) and/or short (μs) pulses, and long and/or short acquisitions can be used depending on the implementation.

Since microbubbles are purely intravascular, their possible locations can be constrained according to a super-resolved vascular map. Acoustic pulses used to disrupt the BBB are typically long, but short echoes can be generated in order to produce super-resolved passive acoustic maps by slightly modulating the transmitted frequency (ultrasonic wave encoding) and isolating the desired frequencies on the receive side. Enforcing constraints such as sparsity and an allowed reconstruction grid (according to the estimated super-resolved vascular map) on the passive acoustic mapping calculations can improve the reconstruction resolution beyond the diffraction limit, revealing details that are missing in conventional passive acoustic maps. These sparsity "priors" may be determined according to the bubble density in each vascular region (in a manner similar to that described in van Sloun et al., "Deep learning in ultrasound imaging," *Proc. of IEEE,* 108(1), 11-29 (2019)). The CEUS and ULM calculations can be aided by information from co-registered vascular maps acquired using different imaging modalities, such as MRI and CT.

CEUS and ULT can also be used to monitor treatment based on vascular changes (vasculature integrity, vasculature diameter changes) by comparing vascular maps and flow velocities and patterns during the treatment to pre-treatment vasculature maps (or maps generated in the course of a prior treatment session). In particular, tracking functional vasculature changes (e.g., the density of functional vessels, a diameter histogram, integrity, and flow patterns) can be used to infer treatment progress and to update acoustic parameters for the treatment. Sampling and comparison of vascular maps may occur between pulses, between multi-pulse sonications, and/or between treatment sessions. The tracked "feature" parameters characterizing functional vasculature changes can be correlated with treatment progress based on conventional machine learning or other techniques, including, for example, linear regression, random forest classification, neural networks, etc. The classifier is trained (or regression coefficients estimated) based on feature parameter values obtained during treatments and the actual progress of treatment as determined by, for example, MRI or CT monitoring and interpretation (which may be manual or automated). Feature parameter values may be obtained in real-time during treatment from short scans and partial vascular information. Similarly, vascular reconstruction can be based on fitting an assumed bubble shape (Errico et al., supra) or relying on the sparsity of the underlying vasculature (see, e.g., van Sloun et al., "Deep learning in ultrasound imaging," *Proc. of IEEE,* 108(1), 11-29 (2019)).

MRI scans and/or CT scans (e.g., CT-angiography), which may be acquired routinely during treatment planning, may alternatively or in addition be used to characterize the vasculature. CT imaging may be performed using contrast agents.

Referring back to FIG. 3A, the method also includes providing, at the target region, microbubbles having a size distribution related to the distribution of vessel diameters (step 312) in accordance with a predetermined relationship. In some embodiments, the distribution of vessel diameters and the microbubble size distribution are histogram distributions having equal numbers of bins (step 314). Additionally, the distribution of vessel diameters and the microbubble size distribution may be histogram distributions having a substantially similar pattern of peaks (step 316). In some embodiments, the providing step 312 includes generating the microbubbles by application of ultrasound at the target region (step 318). In other embodiments, the providing step 312 includes administering the microbubbles as a suspension (step 320). In some embodiments, the distribution of vessel diameters has a peak at approximately 50 μm (step 322).

Referring next to FIG. 3C, in some embodiments, the method also includes detecting (step 330) a characteristic of the microbubbles in the target region. The microbubble characteristic may be detected (step 332) using the ultrasound transducer, an acoustic-signal detection device or a second ultrasound transducer. In some embodiments, the characteristic is (step 334) the presence, size distribution, concentration and/or amount, and/or behavior or response (e.g., cavitation), of the microbubbles. In some embodiments, the method includes determining (step 336) at least one parameter associated with the ultrasound transducer based at least in part on the detected characteristic of the microbubbles, e.g., altering the amplitude of various of the transducer elements to increase or decrease microbubble generation.

A representative end-to-end procedure using microbubbles having a target size distribution is as follows. Prior to and/or during an ultrasound procedure for treating a target tissue region (e.g., by applying sonications to ablate the target), a small cloud of transient microbubbles is provided to the target region to enable focusing, at the target, of the various ultrasound beams produced by transducer elements that will contribute to treatment. The microbubbles may be generated using ultrasound pulses generated by the transducer elements themselves and/or may be introduced intravenously using the administration system 124. Microbubble characteristics (e.g., the presence, concentration and/or amount) and/or behavior or response (e.g., cavitation) are monitored using the acoustic-signal detection device 122 and/or the transducer array 102 during the process of focusing. This process described, for example, in International Application No. PCT/IB2017/000990 (filed on Jul. 19, 2017) and U.S. Patent Application No. 62/781,258 (filed on Dec. 18, 2018); approaches for delivering microbubbles to the target region are provided, for example, in the '1537 PCT application mentioned above; approaches for measuring the characteristics and/or activities of microbubbles are provided, for example, in U.S. Patent Publication No. 2018/0206816 and International Application Nos. PCT/IB2018/000841 (filed on Jun. 29, 2018) and PCT/IB2018/000774 (filed on May 22, 2018); and approaches to configuring the transducer array 102 for detecting microbubble responses are provided, for example, in U.S. Patent Application No. 62/681,282 (filed on Jun. 6, 2018). The entire contents of these applications are incorporated herein by reference.

In one embodiment, after the transducer parameters (e.g., frequencies, phase shifts and/or amplitudes) that optimize the focus at the target region are determined (e.g., via analysis of the acoustic reflections from the microbubbles, as described above), the amount of microbubbles at the target region (and/or nearby non-target region) is preferably limited so as to avoid undesired damage to non-target tissue during ablation of the target tissue. Accordingly, after the focusing procedure, the presence, amount and/or concentration of microbubbles at the target region (and/or nearby non-target region) may be measured based on the acoustic signals transmitted or reflected from the microbubbles using, again, the acoustic-signal detection device 122 and/or transducer array 102. If the microbubbles are present (or, in some embodiments, if the amount thereof exceeds a predetermined threshold that effectively precludes clinically significant damage to target and/or non-target tissue), a microbubble-regulating approach may be implemented to eliminate (or at least reduce) microbubbles at one or more selected non-target regions corresponding to low sensitivity levels on a tissue-sensitivity map; this may then indirectly reduce the microbubble population at the target and/or its nearby region. The size distribution of the microbubbles is controlled as described above.

In various embodiments, properties of the focused beam are optimized based on the characteristics of the microbubbles, including the ability to clear microbubbles. For example, the size and/or shape of the focus may be adjusted to conform to the size and/or shape of the microbubbles that are to be cleared from a target region during an ultrasound procedure. In this way, the microbubble-regulating process may efficiently destroy the selected microbubbles at once. Alternatively, the focus may be shaped/sized to destroy a portion of the microbubbles only. For example, when some of the microbubbles are near an artery wall, cavitation thereof may result in damage to the artery wall; accordingly, the ultrasound controller 108 may shape and size the focus to destroy only a portion of microbubbles that is not in proximity to the artery wall. Adjustment of the focal size and/or shape may be achieved by adjusting the amplification factors and/or the phase shifts of the ultrasound beams transmitted from the transducer elements as described above.

While the main force for distributing microbubbles in the target region and non-target regions outside the target is blood circulation, in some embodiments, the ultrasound transducer can be configured (e.g., by adjusting the phases, amplitudes and/or frequencies) to create a focus that can induce movement of microbubbles by applying an acoustic force thereto. For example, the generated focus may sweep at least a portion of the microbubbles from the target region (or a region having a relatively high sensitivity score) to a lower-sensitivity region (e.g., a facial vein) outside the target. In one embodiment, the generated focus has a relatively low acoustic power that is sufficient to sweep the microbubbles without causing cavitation thereof.

In various embodiments, the focus induces movement of microbubbles by applying an acoustic force thereto. The acoustic force is produced by a change in the density of energy and momentum of the propagating ultrasound waves resulting from absorption, scattering or reflection from the intervening tissue located between the transducer 102 and the target region. Generally, the amplitude of the acoustic force is proportional to the ultrasound intensity. Accordingly, in one implementation, the intensity of the ultrasound beams directed to the microbubbles gradually increases until the generated acoustic force suffices to manipulate and move the microbubbles. In another embodiment, prior to manipulation of the microbubbles, the characteristics (e.g., an absorption coefficient) of the intervening tissue are measured using the imager 112 as described above; the intensity of ultrasound beams sufficient for moving the microbubbles can be computed based thereon. Once the microbubbles are moved away from the target region and/or reach the region (s) having a relatively low sensitivity score, the controller 108 may increase the intensity of the ultrasound beams to cause microbubble cavitation in the low-sensitivity region (s). Since the cavitation now occurs in the low-sensitivity region(s), whatever damage may occur will be clinically acceptable. Accordingly, this approach may advantageously allow microbubbles to be removed from the region that is more vulnerable to the ultrasound-induced microbubble cavitation (e.g., higher-sensitivity region) to the region that is less likely to be damaged by the cavitation (e.g., lower-sensitivity region). As a result, unexpected damage of healthy tissue in the target and/or non-target regions may be minimized.

It should be understood that the terms “point focus” and “line focus,” as used herein, do not refer to points and lines in the strict mathematical sense, but to focus shapes that approximate a point or line, respectively. Thus, the intensity distribution of a point focus (which may, for example, take the shape of a two-dimensional Gaussian distribution) may be characterized by half-widths in both dimensions of the focal plane on the order of a few acoustic wavelengths, whereas the intensity distribution of a line focus (which may, for example, have a one-dimensional Gaussian profile perpendicular to the line) is extended along the direction of the line, but may have a half-width perpendicular thereto on the order of only a few acoustic wavelengths.

In various embodiments, the microbubble characteristic (e.g., the amount, concentration, size distribution, and/or response) during the ultrasound-induced microbubble cavitation at the selected low-sensitivity region(s) and/or during sweeping from the relatively high-sensitivity region toward the relatively low-sensitivity region is monitored in real time using the acoustic-signal detection device 122 and/or the transducer array 102 as described above.

In general, functionality for facilitating a microbubble-mediated ultrasound focusing and treatment procedure and/or using microbubbles to enhance a tissue effect such as reversible BBB opening may be structured in one or more modules implemented in hardware, software, or a combination of both, whether integrated within the controller 108 and/or the administration system 124, or provided by a separate external controller or other computational entity or entities. Such functionality may include, for example, analyzing imaging data of the target and/or non-target regions acquired using an imager 112, determining a 3D voxel set of the target tissue and/or non-target tissue based on the imaging data, determining the anatomical characteristics (e.g., the vascular size distribution) associated with the target/non-target tissue, causing an acoustic-signal detection device and/or transducer array to detect acoustic signals transmitted or reflected from the microbubbles, determining the microbubble amount, concentration, size distribution and/or response based on the detected acoustic signals, comparing the measured microbubble size distribution to a target size distribution and altering the detected size distribution to better conform to the target size distribution, configuring the ultrasound transducer array to generate a focus at the target tissue region, adjusting the ultrasound parameters so as to gradually sweep excess microbubbles from the target region (or nearby non-target region) as necessary, and causing the ultrasound transducer to transmit sonications to the target region for commencing the ultrasound procedure (e.g., BBB opening to facilitate mAb administration), and/or monitoring the microbubble response during the ultrasound procedure, as described above.

In addition, the ultrasound controller 108 and/or controllers associated with the administration system 124 and/or imager 112 may include one or more modules implemented in hardware, software, or a combination of both. For embodiments in which the functions are provided as one or more software programs, the programs may be written in any of a number of high level languages such as PYTHON, FORTRAN, PASCAL, JAVA, C, C++, C#, BASIC, various scripting languages, and/or HTML. Additionally, the software can be implemented in an assembly language directed to the microprocessor resident on a target computer; for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a programmable read-only memory (“PROM”), an erasable programmable read-only memory (“EPROM”), electrically erasable programmable read-only memory (“EEPROM”), field-programmable gate array, or compact disc read-only memory (“CD-ROM”). Embodiments using hardware circuitry may be implemented using, for example, one or more field-programmable gate array (“FPGA”), complex programmable logic device (“CPLD”) or application-specific integrated circuit (“ASIC”) processors.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system for initializing an ultrasound procedure for a target region, the system comprising:

an ultrasound transducer; and a controller configured to:

determine a distribution of vessel diameters of vasculature in the target region; and provide, at the target region, microbubbles having a microbubble size distribution corresponding to the distribution of vessel diameters in accordance with a predetermined relationship, wherein the microbubble size distribution is computed as a function of the distribution of vessel diameters.

2. The system of claim 1, wherein the distribution of vessel diameters and the microbubble size distribution are histogram distributions having approximately equal numbers of bins.

3. The system of claim 2, wherein the bins have heights representing microbubble populations and vessel populations, wherein respective microbubble populations in the bins exceed respective vessel populations in corresponding bins by a factor ranging from $10^2$ to $10^9$.

4. The system of claim 2, wherein the distribution of vessel diameters and the microbubble size distribution are histogram distributions having a substantially corresponding pattern of peaks.

5. The system of claim 1, wherein the predetermined relationship is linear.

6. The system of claim 5, wherein the linear relationship is a ratio of average microbubble diameter to average vessel diameter ranging from 1:3 to 1:30.

7. The system of claim 1, wherein the predetermined relationship is polynomial, exponential, or empirical.

8. The system of claim 1, wherein the distribution of vessel diameters is determined at least in part by contrast-enhanced ultrasound, ultrasound imaging, or super-resolution imaging.

9. The system of claim 1, wherein the microbubble size distribution is a function of a type of microbubbles.

10. The system of claim 1, wherein the providing step comprises generating the microbubbles by application of ultrasound at the target region, or administering the microbubbles as a suspension.

11. The system of claim 1, wherein the target region is a blood-brain barrier.

12. The system of claim 1, wherein the vessels are cortical vessels that range in diameter from 4 μm to less than 100 μm.

13. The system of claim 1, wherein the distribution of vessel diameters has a peak at approximately 50 μm.

14. The system of claim 1, wherein the determining step comprises:

imaging the target region; or identifying the target region and using an atlas to determine the distribution of vessel diameters.

15. The system of claim 1, wherein the controller is further configured to determine at least one parameter associated with the ultrasound transducer for controlling acoustic energy emitted by transducer elements so that the acoustic energy is above a threshold level to thereby induce microbubble generation.

16. The system of claim 15, wherein the at least one parameter associated with the ultrasound transducer comprises at least one of a frequency, an amplitude, or a phase associated with at least one transducer element of the ultrasound transducer.

17. The system of claim 1, further comprising means for detecting a characteristic of the microbubbles in the target region, wherein the means for detecting a characteristic of the microbubbles comprises the ultrasound transducer, an acoustic-signal detection device, or a second ultrasound transducer.

18. The system of claim 17, wherein the characteristic is at least one of a presence, concentration, amount, behavior, and/or response of the microbubbles.

19. The system of claim 17, wherein the controller is further configured to determine at least one parameter associated with the ultrasound transducer based at least in part on the detected characteristic of the microbubbles.

20. A method of performing an ultrasound procedure, the method comprising the steps of:

determining a distribution of vessel diameters of vasculature in a target region;

providing, at the target region, microbubbles having a microbubble size distribution corresponding to the distribution of vessel diameters in accordance with a predetermined relationship, wherein the microbubble size distribution is computed as a function of the distribution of vessel diameters; and administering ultrasound energy to the target region in the presence of the microbubbles.

* * * * *